US011385178B2

(12) United States Patent
Kreifels et al.

(10) Patent No.: US 11,385,178 B2
(45) Date of Patent: *Jul. 12, 2022

(54) DEVICES FOR REAL-TIME POLYMERASE CHAIN REACTION

(71) Applicant: STRECK, INC., La Vista, NE (US)

(72) Inventors: Matthew R. Kreifels, Omaha, NE (US); Scott E. Whitney, Lincoln, NE (US); Gregg Wilder, Strafford, NH (US); John Flanagan, Holbrook, MA (US); James Dowling, New Boston, NH (US); Philip Hills, Deerfield, NH (US); Michael Tilleman, Brookline, MA (US); Jeremie Jackson, Mont Vernon, NH (US)

(73) Assignee: STRECK, INC., La Vista, NE (US)

( * ) Notice: Subject to any disclaimer, the term of this patent is extended or adjusted under 35 U.S.C. 154(b) by 48 days.

This patent is subject to a terminal disclaimer.

(21) Appl. No.: 16/017,507

(22) Filed: Jun. 25, 2018

(65) Prior Publication Data

US 2018/0306719 A1 Oct. 25, 2018

Related U.S. Application Data

(63) Continuation of application No. 14/911,671, filed as application No. PCT/US2014/044858 on Jun. 30, 2014, now Pat. No. 10,006,861.

(Continued)

(51) Int. Cl.
*G01N 21/64* (2006.01)
*G01N 37/00* (2006.01)
(Continued)

(52) U.S. Cl.
CPC ......... *G01N 21/6428* (2013.01); *C12Q 1/686* (2013.01); *G01N 21/645* (2013.01);
(Continued)

(58) Field of Classification Search
CPC ..... B01L 7/52; C12Q 1/686; C12Q 2561/113; C12Q 2563/107; G01N 21/6428; G01N 21/645; G01N 2201/062; G01N 2201/068
See application file for complete search history.

(56) References Cited

U.S. PATENT DOCUMENTS

| D225,526 S | 12/1972 | Baum et al. |
| 3,722,502 A | 3/1973 | Besuner et al. |

(Continued)

FOREIGN PATENT DOCUMENTS

| DE | 4022792 A1 | 2/1992 |
| DE | 102005038252 A1 | 2/2007 |

(Continued)

OTHER PUBLICATIONS

Analytical Biochemistry 186, 328-331 (1990) "Minimizing the Time Required for DNA Amplification by Efficient Heat Transfer to Small Samples".

(Continued)

*Primary Examiner* — Lydia Edwards
(74) *Attorney, Agent, or Firm* — Marshall, Gerstein & Borun LLP

(57) ABSTRACT

An improved device and system for facilitating polymerase chain reaction including a light source, detector, waveguide, and filters that occupy minimal space and facilitate detection of stationary samples, reduced sample read time, and simultaneous reading of multiple light wavelengths.

15 Claims, 4 Drawing Sheets

Related U.S. Application Data

(60) Provisional application No. 61/840,755, filed on Jun. 28, 2013.

(51) Int. Cl.
  *B01L 7/00*  (2006.01)
  *C12Q 1/686*  (2018.01)

(52) U.S. Cl.
  CPC ........... *B01L 7/52* (2013.01); *C12Q 2561/113* (2013.01); *C12Q 2563/107* (2013.01); *G01N 2201/062* (2013.01); *G01N 2201/068* (2013.01)

(56) References Cited

U.S. PATENT DOCUMENTS

| | | |
|---|---|---|
| 3,911,918 A | 10/1975 | Turner |
| D256,053 S | 7/1980 | Steigerwald |
| 4,528,187 A | 7/1985 | Truglio |
| 4,674,640 A | 6/1987 | Asa et al. |
| 4,683,202 A | 7/1987 | Mullis |
| 4,900,321 A | 2/1990 | Kaufman et al. |
| 4,902,624 A | 2/1990 | Columbus et al. |
| D313,098 S | 12/1990 | Boyd |
| 5,084,041 A | 1/1992 | Oxley et al. |
| D330,428 S | 10/1992 | Lewis et al. |
| D337,261 S | 7/1993 | Sherman |
| 5,225,165 A | 7/1993 | Perlman |
| 5,229,327 A | 7/1993 | Farnworth |
| 5,270,011 A | 12/1993 | Altherr |
| 5,304,487 A | 4/1994 | Wilding et al. |
| 5,333,675 A | 8/1994 | Mullis et al. |
| 5,353,186 A | 10/1994 | Ruoss et al. |
| 5,423,792 A | 6/1995 | Oxley |
| 5,455,175 A | 10/1995 | Wittwer et al. |
| 5,475,610 A | 12/1995 | Atwood et al. |
| 5,508,197 A | 4/1996 | Hansen et al. |
| 5,525,300 A | 6/1996 | Danssaert et al. |
| 5,540,892 A | 7/1996 | Kidd et al. |
| 5,571,479 A | 11/1996 | Koch |
| 5,576,218 A | 11/1996 | Zurek et al. |
| 5,598,349 A | 1/1997 | Elliason et al. |
| 5,604,101 A | 2/1997 | Hanley et al. |
| 5,656,493 A | 8/1997 | Mullis et al. |
| 5,674,742 A | 10/1997 | Northrup et al. |
| 5,681,741 A | 10/1997 | Atwood et al. |
| 5,683,659 A | 11/1997 | Hovatter |
| 5,721,136 A | 2/1998 | Finney et al. |
| 5,795,547 A | 8/1998 | Moser et al. |
| 5,832,543 A | 11/1998 | Bosserman |
| 5,856,174 A | 1/1999 | Lipshutz et al. |
| 5,863,791 A | 1/1999 | Baldszun et al. |
| 5,928,880 A | 7/1999 | Wilding et al. |
| 5,928,907 A | 7/1999 | Woudenberg et al. |
| 5,935,858 A | 8/1999 | Herst |
| 5,958,349 A | 9/1999 | Petersen et al. |
| 5,972,716 A | 10/1999 | Ragusa et al. |
| 6,015,534 A | 1/2000 | Atwood |
| D425,625 S | 5/2000 | Niermann |
| 6,140,613 A | 10/2000 | Tsuno |
| 6,144,448 A | 11/2000 | Mitoma |
| 6,159,727 A | 12/2000 | Bochkariov |
| 6,174,670 B1 | 1/2001 | Wittwer et al. |
| 6,210,382 B1 | 4/2001 | Hogg |
| 6,210,958 B1 | 4/2001 | Brust et al. |
| 6,303,343 B1 | 10/2001 | Kopf-Sill |
| 6,312,886 B1 | 11/2001 | Lee et al. |
| 6,372,486 B1 | 4/2002 | Fripp |
| 6,372,895 B1 | 4/2002 | Bentsen et al. |
| 6,374,684 B1 | 4/2002 | Dority |
| 6,392,241 B1 | 5/2002 | Rushbrooke et al. |
| 6,472,186 B1 | 10/2002 | Quintanar et al. |
| 6,503,750 B1 | 1/2003 | Benett et al. |
| 6,556,940 B1 | 4/2003 | Tretiakov et al. |
| 6,558,947 B1 | 5/2003 | Lund et al. |
| 6,645,191 B1 | 11/2003 | Knerr et al. |
| 6,657,169 B2 | 12/2003 | Brown |
| 6,734,401 B2 | 5/2004 | Bedingham et al. |
| 6,780,617 B2 | 8/2004 | Chen |
| 6,783,025 B2 | 8/2004 | Lohn |
| 6,783,736 B1 | 8/2004 | Taylor et al. |
| 6,787,338 B2 | 9/2004 | Wittwer et al. |
| 6,814,934 B1 | 11/2004 | Higuchi |
| 6,818,185 B1 | 11/2004 | Petersen et al. |
| 6,875,602 B2 | 4/2005 | Gutierrez |
| 6,881,541 B2 | 4/2005 | Petersen et al. |
| 6,887,693 B2 | 5/2005 | McMillan et al. |
| 6,889,468 B2 | 5/2005 | Bedingham et al. |
| 6,964,862 B2 | 11/2005 | Chen |
| 6,987,253 B2 | 1/2006 | Bedingham et al. |
| 7,051,536 B1 | 5/2006 | Cohen et al. |
| 7,081,600 B2 | 7/2006 | Brown et al. |
| 7,138,254 B2 | 11/2006 | Jovanovich et al. |
| 7,164,077 B2 | 1/2007 | Venkatasubramanian |
| 7,164,107 B2 | 1/2007 | Bedingham et al. |
| 7,189,252 B2 | 3/2007 | Krueger |
| 7,238,321 B2 | 7/2007 | Wittwer et al. |
| 7,255,833 B2 | 8/2007 | Chang et al. |
| 7,295,316 B2 | 11/2007 | Boege et al. |
| 7,315,376 B2 | 1/2008 | Bickmore, Jr. et al. |
| 7,422,905 B2 | 9/2008 | Clague et al. |
| 7,435,933 B2 | 10/2008 | Bedingham et al. |
| 7,439,069 B2 | 10/2008 | Nippoldt et al. |
| 7,442,542 B2 | 10/2008 | Miao et al. |
| 7,462,323 B1 | 12/2008 | Chang et al. |
| 7,482,116 B2 | 1/2009 | Birnboim |
| 7,490,976 B2 | 2/2009 | Bucher |
| 7,507,575 B2 | 3/2009 | Bedingham et al. |
| 7,544,506 B2 | 6/2009 | Breidford et al. |
| 7,578,976 B1 | 8/2009 | Northrup et al. |
| 7,648,095 B2 | 1/2010 | Jagle |
| 7,749,452 B2 | 7/2010 | Brem et al. |
| D621,520 S | 8/2010 | Talmer et al. |
| D621,951 S | 8/2010 | Bucholtz et al. |
| D640,795 S | 6/2011 | Jackson et al. |
| 8,003,370 B2 | 8/2011 | Maltezos et al. |
| 8,008,046 B2 | 8/2011 | Maltezos et al. |
| 8,137,616 B2 | 3/2012 | Sagner et al. |
| 8,889,086 B2 | 11/2014 | Viljoen et al. |
| 9,034,635 B2 | 5/2015 | Termaat et al. |
| 9,737,891 B2 | 8/2017 | TerMaat et al. |
| 9,932,632 B2 | 4/2018 | Kreifels et al. |
| 10,006,861 B2 | 6/2018 | Kreifels et al. |
| 2001/0007759 A1 | 7/2001 | Wittwer et al. |
| 2002/0030044 A1 | 3/2002 | Brown |
| 2002/0086417 A1 | 7/2002 | Chen |
| 2004/0122559 A1 | 6/2004 | Young et al. |
| 2004/0214315 A1 | 10/2004 | Saluz et al. |
| 2005/0009070 A1 | 1/2005 | Arciniegas et al. |
| 2005/0151972 A1 | 7/2005 | Boege et al. |
| 2005/0282270 A1 | 12/2005 | Shin et al. |
| 2006/0088931 A1 | 4/2006 | Ririe |
| 2006/0101830 A1 | 5/2006 | Cohen et al. |
| 2006/0160243 A1 | 7/2006 | Tang et al. |
| 2006/0223169 A1 | 10/2006 | Bedingham et al. |
| 2006/0228264 A1 | 10/2006 | Garvin et al. |
| 2007/0051739 A1 | 3/2007 | Giraud |
| 2007/0098594 A1 | 5/2007 | Elkin et al. |
| 2007/0111206 A1 | 5/2007 | Tyagi et al. |
| 2007/0128080 A1 | 6/2007 | Lohn |
| 2007/0140919 A1 | 6/2007 | Clarkson et al. |
| 2007/0262265 A1 | 11/2007 | MacCraith et al. |
| 2008/0003649 A1 | 1/2008 | Maltezos et al. |
| 2008/0038813 A1 | 2/2008 | Chen |
| 2008/0061429 A1 | 3/2008 | Cohen et al. |
| 2008/0193912 A1 | 8/2008 | Fong et al. |
| 2008/0219889 A1 | 9/2008 | Schaefer et al. |
| 2008/0248534 A1 | 10/2008 | Lim et al. |
| 2009/0011417 A1 | 1/2009 | Maltezos et al. |
| 2009/0023603 A1 | 1/2009 | Selden et al. |
| 2009/0061450 A1 | 3/2009 | Hunter |
| 2009/0120104 A1 | 5/2009 | Federer |
| 2009/0136385 A1 | 5/2009 | Handique et al. |
| 2009/0155838 A1 | 6/2009 | Hale |

(56) References Cited

U.S. PATENT DOCUMENTS

| | | |
|---|---|---|
| 2009/0162866 A1 | 6/2009 | Birnboim |
| 2009/0275113 A1 | 11/2009 | Maltezos et al. |
| 2010/0137166 A1 | 6/2010 | Kain et al. |
| 2010/0285571 A1 | 11/2010 | Coursey et al. |
| 2010/0288059 A1 | 11/2010 | Viljoen et al. |
| 2010/0291536 A1 | 11/2010 | Viljoen et al. |
| 2011/0039305 A1 | 2/2011 | Termaat et al. |
| 2011/0311978 A1 | 12/2011 | Makarewicz, Jr. et al. |
| 2012/0014835 A1 | 1/2012 | Howell et al. |
| 2012/0295268 A1 | 11/2012 | Furlan |
| 2012/0308990 A1 | 12/2012 | TerMaat et al. |
| 2014/0045250 A1 | 2/2014 | Kreifels et al. |
| 2015/0238968 A1 | 8/2015 | TerMaat et al. |
| 2017/0065971 A1 | 3/2017 | Kreifels et al. |
| 2017/0304828 A1 | 10/2017 | TerMaat et al. |
| 2018/0223335 A1 | 8/2018 | Kreifels et al. |

FOREIGN PATENT DOCUMENTS

| | | |
|---|---|---|
| EP | 0350675 A2 | 1/1990 |
| EP | 0580362 A1 | 1/1994 |
| EP | 1000661 A1 | 5/2000 |
| EP | 1757367 A1 | 2/2007 |
| EP | 1962084 A1 | 8/2008 |
| EP | 2193845 A1 | 6/2010 |
| EP | 2255010 A1 | 12/2010 |
| EP | 2739747 A1 | 6/2014 |
| WO | WO-98/43740 A2 | 10/1998 |
| WO | WO-01/15680 A1 | 3/2001 |
| WO | WO-02/41999 A1 | 5/2002 |
| WO | WO-2004/052527 A1 | 6/2004 |
| WO | WO-2005/113741 A1 | 12/2005 |
| WO | WO-2006/024879 A1 | 3/2006 |
| WO | WO-2006/073811 A2 | 7/2006 |
| WO | WO-2009/009124 A1 | 1/2009 |
| WO | WO-2009/105499 A1 | 8/2009 |
| WO | WO-2010/079338 A2 | 7/2010 |
| WO | WO-2010/091400 A2 | 8/2010 |
| WO | WO-2010/132756 A2 | 11/2010 |
| WO | WO-2010/132800 A1 | 11/2010 |
| WO | WO-2011/082415 A2 | 7/2011 |
| WO | WO-2011/086497 A2 | 7/2011 |
| WO | WO-2011/153244 A1 | 12/2011 |
| WO | WO-2012/166913 A1 | 12/2012 |
| WO | WO-2013/087446 A1 | 6/2013 |
| WO | WO-2014/025398 A1 | 2/2014 |
| WO | WO-2015/134053 A1 | 9/2015 |

OTHER PUBLICATIONS

Australian Patent Application No. 2014302052, Examination Report No. 1, dated Aug. 24, 2017.
Boshoff-Mostert et al., Crack propagation in catalytic pellets due to thermal stresses. AICHE J. Aug. 1996, 2288-2294, 42.
Chaisson et al., Tuberculosis in Africa—Combating an HIV driven crisis. N. Engl. J. Med., Mar. 13, 2008, 1089-1092, 358(11).
Davies et al., The diagnosis and misdiagnosis of tuberculosis, Int. J. Tuberc. Lung. Dis., Nov. 2008, 1226-1234, 12(11).
Davis et al., The rheological properties of sputum, Biorheology, Apr. 1969, 11-21, 6(1).
Dziadek et al., Specificity of insertion sequence-based PCR assays for *Mycobacterium tuberculosis* complex, Int. J. Tuberc. Lung. Dis., Jan. 2001, 569-574, 5(6).
El-Hajj et al., Detection of rifampin resistance in *Mycobacterium tuberculosis* in a single tube with molecular beacons, J. Clin. Microbiol., Nov. 2001, 4131-4137, 39(11).
European Application No. 14745274.2, Communication Pursuant to Article 94(3) EPC, dated Dec. 22, 2017.
European Application No. 14745274.2, Communication Pursuant to Article 94(3) EPC, dated May 16, 2017.
Flores et al., In-house nucleic acid amplification tests for the detection of *Mycobacterium tuberculosis* in sputum specimens: meta-analysis and meta-regression, BMC Microbiol., Oct. 2005, 55, 5.
Friedman, Neal A., et al., "Capillary tube resistive thermal cycling", Anal. Chem., 1998, 2997-3002.
Global Health Diagnostics Forum, The right tools can save lives, Nature, Dec. 7, 2006, 681, 444.
Greco et al., Current evidence on diagnostic accuracy of commercially based nucleic acid amplification tests for the diagnosis of pulmonary tuberculosis, Thorax, Sep. 2006, 783-790, 61(9).
Griep et al., Kinetics of the DNA *Polymerasepyrococcus kodakaraensis*. Chemical Engineering Science, 2006, 3885-3892, 61.
International Preliminary Report on Patentability from the European Patent Office for Application No. PCT/US2014/044858, dated Jan. 7, 2016.
International Search Report and Written Opinion from the European Patent Office for Application No. PCT/US2014/044858, dated Nov. 10, 2014.
Keeler et al., Reducing the global burden of tuberculosis: The; contribution of improved diagnostics, Nature, Nov. 23, 2006, 49-57, 444 Supp. 1.
Marras et al., Genotyping SNPs with molecular beacons, Methods Mol. Biol. 2003, 111-128, 212.
McEvoy et al., The role of IS6110 in the evolution of *Mycobacterium tuberculosis*, Tuberculosis (Edinb)., Sep. 2007, 393-404, 87(5).
Menzies et al., Risk of tuberculosis infection and disease associated with work in health care settings, Int. J. Tuberc. Lung Dis., Jun. 2007, 593-605, 11(6).
Menzies et al., Tuberculosis among health care workers, N. Engl. J. Med., Jan. 12, 1995, 92-98, 332(2).
Musser, Antimicrobial agent resistance in mycobacteria; genetic insights, Clin. Microbiol. Rev., Oct. 1995, 496-514, 8(4).
Muthupillai et al., Magnetic resonance elastography by direct; visualization of propagating acoustic strain waves, Science,; Sep. 29, 1995, 1854-1857, 269.
Negi et al., Diagnostic potential of IS6110, 38kDa, 65kDa and 85B sequence-based polymerase chain reaction in the diagnosis of *Mycobacterium tuberculosis* in clinical samples, Indian. J. Med. Microbiol. Jan. 2007, 43-49, 25(1).
Nielsen et al., Elastic contributions dominate the viscoelastic properties of sputum from cystic fibrosis patient, Biophys. Chem., Dec. 20, 2004, 193-200, 112.
Northrup, M. Allen, et al., "A miniature integrated nucleic acid analysis system", Automation Technologies for Genome Characterization, 1997, pp. 189-204.
Othman et al., Microscopic magnetic resonance elastography (muMRE), Magnetic Resonance in Medicine, Sep. 2005, 605-615, 54.
Perkins et al., Progress towards improved tuberculosis diagnostics for developing countries, Lancet, Mar. 18, 2006, 942-943, 367.
Potentially Related U.S. Appl. No. 61/681,879, filed Aug. 10, 2012.
Potentially Related U.S. Appl. No. 61/752,494, filed Jan. 15, 2013.
Ramaswamy et al., Molecular genetic basis of antimicrobial agent resistance in *Mycobacterium tuberculosis*: 1998 update, Tuber. Lung Dis., 1998, 3-29, 79.
Riska et al., Molecular determinants of drug resistance in tuberculosis, Int. J. Tuberc. Lung Dis., Feb. 2000, S4-10, 4(2 Suppl 1).
Sarmiento et al., Assessment by meta-analysis of PGR for diagnosis of smear-negative pulmonary tuberculosis, J. Clin. Microbiol., Jul. 2003, 3233-3240, 41(7).
Shah et al., Extensively Drug-Resistant Tuberculosis in the United States 1993-2007, JAMA, Nov. 12, 2008, 2153-2160, 300(18).
Singh et al., Comparative evaluation of FASTPlaque assay with PCR and other conventional in vitro diagnostic methods for the early detection of pulmonary tuberculosis, J. Clin. Lab. Anal., 2008, 367-374, 22(5).
Somoskovi et al., The molecular basis of resistance to isoniazid, rifampin, and pyrazinamide in *Mycobacterium tuberculosis*, Respir. Res., 2001, 164-168, 2(3).
Storla et al., A systematic review of delay in the diagnosis and treatment of tuberculosis, BMC Public Health, Jan. 14, 2008, 15, 8.
Sun et al., Comparison of gyrA gene mutations between laboratory-selected ofloxacin-resistant *Mycobacterium tuberculosis* strains and clinical isolates, Int. J. Antimicrob. Agents., Feb. 2008, 115-112, 31(2).

(56) References Cited

OTHER PUBLICATIONS

Telenti, Genetics and pulmonary medicine. 5. Genetics of drug resistant tuberculosis, Thorax, Sep. 2008, 793-797, 53.

Thierry et al., Characterization of a *Mycobacterium tuberculosis* insertion sequence, IS6110, and its application in diagnosis, J. Clin. Microbiol., Dec. 1990, 2668-2673, 28(12).

Valente et al., A kinetic study of in virto lysis of *Mycobacterium smegmatis*, Chemical Engineering Science, 2009, 1944-1952, 64.

Van Soolingen et al., Comparison of various repetitive DNA elements as genetic markers for strain differentiation and epidemiology of *Mycobacterium tuberculosis*, J. Clin. Microbiol., Aug. 1993, 19871995, 31.

Viljoen et al., A macroscopic kinetic model for DNA polymerase elongation and the high-fidelity nucleotide selection, Computational Biology and Chemistry, Apr. 2005, 101-110, 29.

Wang et al., Fluoroquinolone resistance in *Mycobacterium tuberculosis* isolates: associated genetic mutations and relationship to antimicrobial exposure, J. Antimicrob. Chemother., May 2007, 860-865.

World Health Organization, Global tuberculosis control—epidemiology, strategy, financing, WHO Report 2009, WHO/HTM/TB/2009.411.

Guo et al., "CMOS Time-Resolved, Contact, and Multispectral Fluorescence Imaging for DNA Molecular Diagnostics," Sensors 14(11):20602-20619 (2014).

Maruyama et al., "An All-Digital, Time-Gated 128×128 Spad Array for On-Chip, Filter-Less Fluorescence Detection," 2011 16th International Solid-State Sensors, Actuators and Microsystems Conference, Beijing, China 1180-1183 (2011).

Palubiak et al., "High-Speed, Single-Photon Avalanche-Photodiode Imager for Biomedical Applications," IEEE Sensors Journal 11(10:2401-2412 (2011).

DEVICES FOR REAL-TIME POLYMERASE CHAIN REACTION

CROSS-REFERENCE TO RELATED APPLICATIONS

This application is a Continuation of U.S. application Ser. No. 14/911,671, filed Feb. 11, 2016, which is a U.S. National Stage of International Application No. PCT/US14/44858, filed Jun. 30, 2014, which claims the benefit of U.S. Provisional Application Ser. No. 61/840,755 filed Jun. 28, 2013, which are hereby incorporated by reference in their entirety.

FIELD OF THE INVENTION

The present invention relates generally to devices and systems for facilitating polymerase chain reactions.

BACKGROUND OF THE INVENTION

A number of optical detection systems have been developed for use in qualitative and quantitative nucleic acid measurements. Many such systems involve the use of fluorescent probes or dyes in which the resulting signal intensities are generally proportional to the reaction products of polymerase chain reaction (PCR) amplification.

As an example, U.S. Pat. No. 5,928,907 describes a system for facilitating real-time fluorescence-based measurements of nucleic acid amplification products utilizing a lens co-axially disposed with a fiber optic cable for focusing a single color excitation beam into the volume of a sample. U.S. Pat. No. 6,144,448 describes a fluorescence detecting device including direct fiber optic connections between a single light source, container holder and single fluorescence detector. U.S. Pat. No. 7,295,316 describes a fluorometry device including a light source for providing a source beam and optical devices for filtering the source beam. The optical devices are located on a movable platform and the devices filter fluorescent light from the samples and also separate the source beam from the fluorescent light. U.S. Pat. No. 7,315,376 describes a sample holder provided together with an optical manifold having an excitation source, a photo receiver, or both, for each sample. U.S. Pat. No. 7,507,575 describes a data acquisition device and a detection device coupled to the data acquisition device. The detection device includes a plurality of removable optical modules and a rotating disk having a plurality of process chambers having a plurality of species that emit fluorescent light at different wavelengths. U.S. Pat. No. 8,137,616 describes a system for performing multi-color real time PCR, comprising a flexible real time PCR instrument and a specific composition or reaction mixture for performing multiplex PCR. U.S. Publication No. 2012/0295268 describes detection instruments including filters that provide both emission and detection functions.

There remains a need for an improved system and device for facilitating polymerase chain reaction that allows for detection of stationary samples, reduced sample read time and simultaneous reading of multiple light wavelengths, resulting in an increase in the speed with which amplification and quantification take place. There is a further need for instruments that include multiple light sources and detectors that occupy minimal space and require little or no ancillary instrumentation for facilitating light provision, fluorescence detection, or movement of samples to read different samples or fluorescent wavelengths. There is also a need for instruments that facilitate PCR and detection without direct connection between a sample holder and fiber optic cable.

SUMMARY OF THE INVENTION

The present teachings meet one or more of the above needs by providing an instrument for performing polymerase chain reaction with real-time detection, including a light source, detector, waveguide, and filter sets that occupy minimal space and facilitate detection of stationary samples, reduced sample read time, and simultaneous reading of multiple light wavelengths.

The present teachings further provide for an instrument for performing polymerase chain reaction with real-time detection comprising a filter wheel including a plurality of filter pairs wherein one filter in each pair is an emission filter and one filter in each pair is a detection filter and wherein no filters align with both an emission light path and a detection light path.

The present teachings further provide for a device for performing polymerase chain reaction with real-time detection comprising a sample holder configured to receive one or more sample tubes that each have at least one portion that is generally optically transparent. The sample tubes are each adapted to receive a biological sample having a nucleic acid to be amplified and at least one fluorescing agent that interacts with the nucleic acid during amplification and that emits light upon excitation by light of a known wavelength. The device further includes at least one light emitting diode device that is carried on at least one support substrate, is in electrical communication with a power source, and is adapted to emit light at a plurality of different wavelengths. The device may also include at least one photodiode array detector adapted to issue signals based upon intensity of light it receives and a filter wheel including at least one filter pair such that one filter in each pair is an emission filter and one filter in each pair is a detection filter. The instrument may be free of any filter that is both and emission filter and a detection filter. Each filter may allow two or more bands of light wavelengths to pass. The instrument may be free of any filters that allow only a single band of light wavelength to pass. One of each filter pair may include one filter that is exclusively an emission filter and one filter that is exclusively a detection filter. The instrument may be free of any filters that are not exclusively emission filters or detection filters. The number of filters may match exactly the number of fluorophore classes detected by the instrument. The instrument may be free of any filters that must align with both an emission light path and a detection light path. One or more filters may not align with both an emission light path and a detection light path. All filters may not align with both an emission light path and a detection light path.

As will be seen, the instrument described herein offers a unique approach to providing a modular PCR device providing relatively high-speed PCR amplification and detection by virtue of the device's ability to provide solid-state detection of stationary samples and reduced sample read time, and the ability to simultaneously detect light at multiple wavelengths.

DETAILED DESCRIPTION

Figure 1:
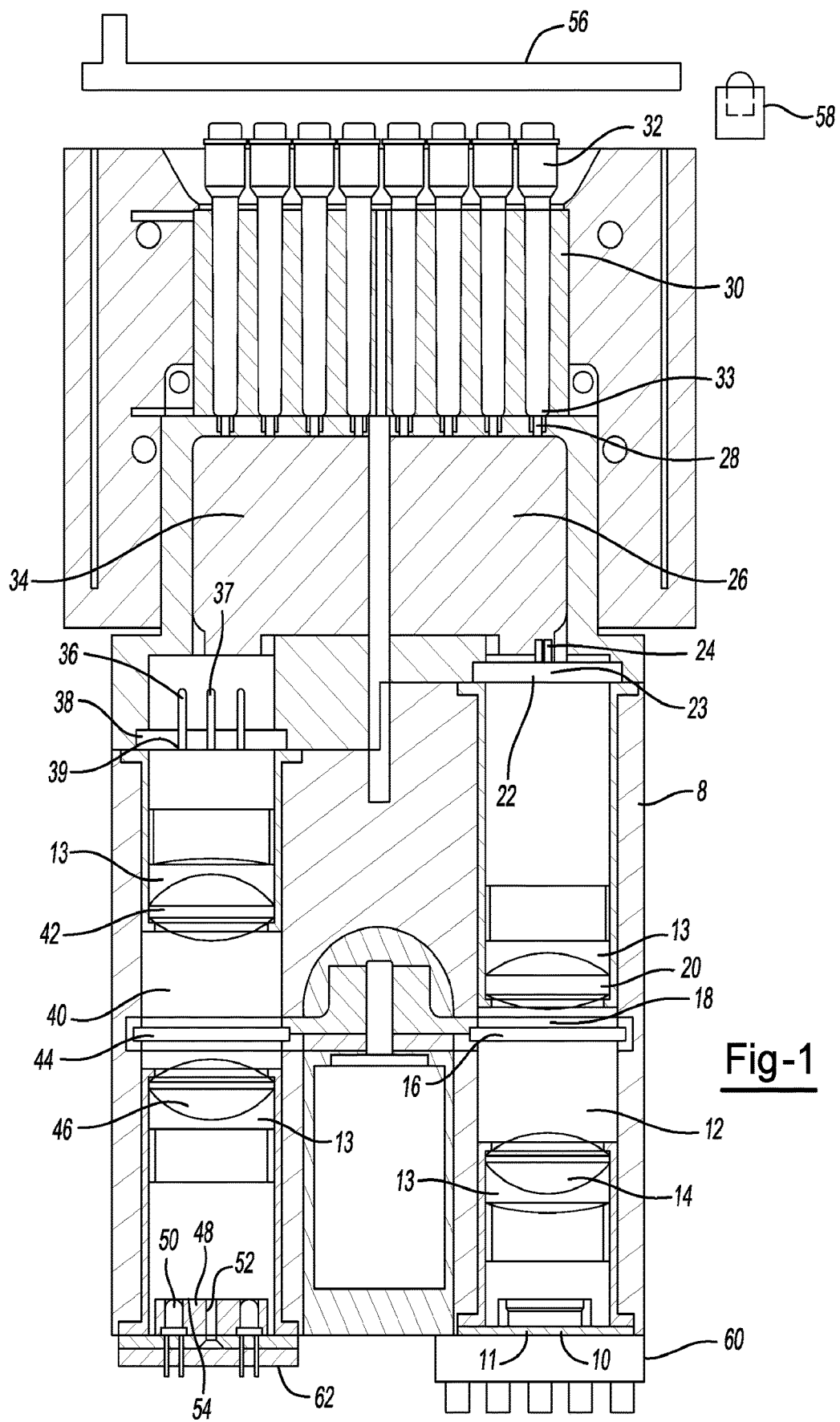
FIG. 1 is a side cutaway view of an illustrative real-time cycling module in accordance with the present teachings.

This application is related to and claims the benefit of the filing date of U.S. Provisional Application Ser. No. 61/840,755 filed Mar. 28, 2013, the contents of this application being hereby incorporated by reference for all purposes.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

This application is also related to U.S. Provisional Application No. 61/681,879 filed Aug. 10, 2012 and U.S. Provisional Application No. 61/752,494, filed Jan. 15, 2013. This application is also related to U.S. application Ser. No. 13/484,963 filed May 31, 2012 and Ser. No. 13/833,349 filed Mar. 15, 2013. The contents of the aforementioned applications are hereby incorporated by reference for all purposes.

The present teachings pertain generally to an improved device for performing high-speed real-time polymerase chain reaction. The device includes one or more PCR modules, each PCR module including one or more light sources, one or more detectors, one or more waveguide devices and optical componentry for light differentiation. Advantages of the instrument described herein include reduced total componentry which allows for interchangeability of PCR modules and a reduced footprint. This includes the ability to employ less hardware per sample. Further, minimal hardware is required per sample such that the functionality of the components described herein is maximized over a wider number of samples. As a specific example, the instrument described herein may require only one light source (or one light source component) for multiple samples. In addition, the present teachings provide for the emission and detection of multiple colors for multiplex PCR, and for the ability to give each fluorescent agent an intense specific light color that more closely matches the fluorescent agent's peak light absorption wavelengths. Further, detecting from the bottom of one or more samples as taught herein may leave side walls of the sample tubes available for maximum heat flow/thermal control and the top of the sample tubes available for simplified sample access. The multiple module arrangement of the present teachings also allows for on-demand instrument availability and increased sample throughput. The inclusion of multiple samples per module allows for each sample to be given a nearly identical thermal profile to better perform statistical comparisons of multiple samples.

The thermocycler instruments of the teachings herein follow the basic principles of WO/2009/105499 and U.S. application Ser. No. 12/918,594 (U.S. Publication No. 2011/0039305) and Ser. No. 13/484,963 in that a sample block (e.g., a sample holder) is sandwiched between opposing thermoelectric devices. The teachings, however, address a number of new features for thermocycler instruments that successfully and unexpectedly improve efficiency and operation of the instruments as compared with instruments that do not employ such features. The teachings further provide for thermocycler instruments that facilitate simultaneous amplification and quantification of nucleic acids.

The mounting of the sample block between the thermoelectric devices allows for more thermal uniformity within and among the sample bores (e.g., sample holder) within the sample block for receiving samples. Specifically, precisely how the sample block is mounted in between the thermoelectric devices can greatly affect the variance of temperatures experienced within each sample bore. Direct contact, indirect contact or close proximity of any components to the silver block (with the exception of the thermoelectric devices, thermal heat transfer compound, and/or thermal heat transfer pads) can cause temperature variance among the bores of the sample block. Contact between the sample block and any other devices can cause temperature variance of greater than 1° C. or even greater than 3° C. from one sample well to another or from one portion of the well to another portion of the same well. Locating the sample block such that it is "floating" between the thermoelectric devices such that direct contact is between the sample block and thermoelectric devices is limited, can result in improved uniformity. For example, the variance between the sample bores can be less that 2° C. or even less than 1° C. For example, in U.S. Pat. No. 6,144,448 an optical fiber is physically connected to the sample holder; this physical connection causes significant heat loss and well-to-well temperature variations as heat travels from the sample holder through the physical connection to the optical fiber, and potentially down the optical fiber. In the "floating" sample holder design, the only contact to the sample holder is the thermoelectric devices and any heat transfer compounds or pads necessary to facilitate heat transfer between the sample holder and the thermoelectric devices. The sample holder in the present invention is placed near the optical detection components in order to minimize light loss; however, a ~0.084 mm air gap is placed between the sample holder and any optical component in order to avoid conductive heat loss and related thermal non-uniformity issues caused by direct physical connections.

The nature of the sample block being sandwiched between opposing thermoelectric devices requires that samples located within the sample block receive light from a light source from either above or below the sample holder, given the difficulty with transmitting light through the thermoelectric devices. As a further result of the sandwich design, detection must also occur from above or beneath the sample holder. It is also possible that the fiber optics may be integrated into the sample block.

The device may utilize a number of components. Preferably, a light source is utilized within the instrument. The light source may be located within the instrument such that it provides light through one or more optically clear portions of a tube in which a sample is located. The light source may be located on a printed circuit board. The printed circuit board may thus provide an electrical supply to the light source. The light source may include one or more light emitting diodes (LEDs). In the event that the instrument contains more than one sample block, each sample block may include its own light source. Each sample block may have multiple light sources, with one or more light sources for each sample well or a shared light source among wells (e.g. one light source optically connected to two or more sample wells). Each light source may be carried on a common substrate. Further, each light source may include a plurality of distinct lights such that each distinct light provides light at a different wavelength. As an example, each sample block may include an array of LED lights, each array including distinct lights at one, two, three, four, or more different wavelengths in order to better match the peak optical absorption wavelengths of various fluorescent agents. In this case, the LED light sources may be grouped underneath a forked fiber optic waveguide such that one or more light sources enter the same fiber optic fork. In this case, a plurality of high power LEDs (of wavelengths typically covering the 400 nm to 700 nm visible light region) may be grouped together with the light generation diode region in an area less than about 3 mm by 5 mm (an example of which is available from Philips Lumileds Lighting Company under the designation Luxeon Z). One such grouping may include four Luxeon Z LEDs with wavelength peaks of approximately 477.5 nm, 522.5 nm, 585.5 nm, and 665.0 nm. A second such grouping may include four Luxeon Z LEDs with wavelength peaks of approximately 447.5 nm, 494.0 nm, 537.5 nm, and 635.0 nm. One such grouping may include six Luxeon Z LEDs with wavelength peaks of approximately 477.5 nm, 527.5 nm, 532.5 nm, 588.5 nm, 630.0 nm, and 660.0 nm (all peaks ±10 nm due to normal LED manufacturing variation). One such grouping may include six Luxeon Z LEDs with wavelength peaks of approximately 477.5 nm, 527.5 nm, 567.5 nm, 588.5 nm, 630.0 nm, and 660.0 nm (all peaks ±10 nm due to normal LED manufacturing variation). Two or more such groupings may be incorporated in each module with each grouping having its own fork of the fiber optics waveguide and optionally its own multi-band bandpass filter. Alternatively, each LED light source may include only 1 distinct light adapted to emit a plurality of different wavelengths. In this case, a plurality of LEDs (each of different wavelength) may be encapsulated behind a single lens within a single assembly (an example of which is available from LED ENGIN, Inc., under the designation LZ4-00MA00). Each compact grouping or single assembly of LEDs may be considered as a light emitting diode device.

The light source may be part of an assembly that includes a carrier having a first surface and a generally opposing second surface. The light emitting diode may be exposed via the first surface. One or more electrical contacts (e.g., pads) may be located on or as part of the second surface and be in electrical communication with the diode. In this manner, the pads may be applied to a substrate (e.g., by way of a soldering to a printed circuit board). The upper surface may include one or more apertures through which the light may be emitted from the LEDs. The upper surface may include one or more conduits of a predetermined depth (e.g. about 1 mm, 2 mm, 3 mm, 4 mm, 5 mm or higher) that may be suitably adapted to connect in light transmission relationship with a wave guide structure (e.g., a fiber optic structure). The conduits may be elongated and include a longitudinal axis. They may be generally cylindrical. They may be at least partially conical. They may include a generally round, oval, triangular, rectangular or other polygonal cross-sectional profile relative to the longitudinal axis. They may have a wall structure defining a passage in the conduit that has a taper (e.g., less than about 15, 10, or even 5°, though tapers of at least 20, 30 or 45° are possible) relative to the longitudinal axis.

The light source will typically include an exposed end through which light is emitted. For each light source of a predetermined wavelength, the end may have an area that is smaller than about 9 mm$^2$, 6 mm$^2$, or even 3 mm$^2$. It may have an area that is larger than about 0.5 mm$^2$, 1 mm$^2$, or even 2 mm$^2$. The emitted beam may have an emission axis, and may exhibit a generally linear, rectangular, oval, circular, or other cross-sectional profile relative to the emission axis.

The light source may exhibit one or any combination of performance characteristic as set forth in the LUXEON Z Datasheet DS105 20120916, incorporated by reference herein (without limitation, pages 3 through 9, page 14-20, and 24 through 27). The light source may exhibit one or any combination of structural characteristics as set forth in the LUXEON Z Datasheet DS105 20120916, incorporated by reference herein (without limitation, pages 10 through 13 and 21 through 23).

The light source may be a relatively high power light source which may provide for more sensitive detection capability. As an example, the light source may be rated at a total of 15 Watt, 30 Watt, or 40 Watts or more, although the light source may or may not be operated at the maximum level. As a result of the high power of the light source, it may be capable of dissipating heat. The light source may thus be in close thermal communication with a heat sink, which may be located onto the printed circuit board. The heat sink may be located beneath, and/or around the light source. The heat sink may assist in dissipating heat from the light source.

An additional benefit of LEDs is that they use less power than other types of light sources (e.g., compact fluorescent or incandescent bulbs) per unit of light generated. LEDs also have improved durability as compared to other light sources. In addition, the use of LEDs as the light source allows for compact packaging for insertion into small spaces within the instrument. Preferably the packaging for the light source may be less than 1 cm on each side, or even less than 0.8 cm on each side. The light source may be a grouping of LEDs with the grouping being less than 1 cm on each side, or even less than 5 mm on each side. As a result. LEDs allow for effective output and performance from a device that occupies minimal space. In one embodiment, the light source can be located beneath the heat exchangers. In an alternative embodiment, the light source may be located above the sample block. In the event that the fiber optics are flexible, the light source may be located anywhere depending upon the arrangement of the samples and the nature of the tubes containing the samples. The small packaging of the light source assists in maintaining the small, lightweight and portable nature of the instrument.

The selected light source should be compact, compatible with any fiber optics design, and sufficiently bright. In the event that LEDs are selected as the light source, it may be beneficial for multiple LED elements to be located into a single housing. For example, a single housing may include at least 4, at least 8, or even at least 12 LED elements such as the LuxiGen family of LEDs available from LED Engin, San Jose, Calif. Any LED lens may be formed with a flat top for improved connection to any fiber optic cable. Ultra-small LEDs may be utilized such as Luxeon Z LEDs, Phillips Lumileds Lighting Company, San Jose, Calif. or XLamp LEDs from Cree, Morrisville, N.C. These ultra-small LED's may be compactly grouped together. A four-color LED grouping may be utilized as the light source. An eight-color LED combination may be utilized as the light source.

The instrument may also include a device for detecting a reaction within a sample. The detector may include a photodiode array which issues a signal proportionally based upon intensity of light it receives. An example of a photodiode is the Taos TSL 1402R, available from AMS-TAOS USA Inc., Plano, Tex. The detector may be located within less than about 10 mm, less than about 5 mm, or even less than about 3 mm from an end of a waveguide to help avoid light from becoming diffuse. The detector may be located in an isolated contained chamber so that it is not exposed to any other light source and is insulated from heat generated by the rest of the instrument. The chamber may be formed as a surrounding wall structure that substantially insulates the detector from other light. The detector may be formed as an individual array for each sample or alternatively may be a single array subdivided into array portions that are dedicated to individual samples. The detector may be formed as arrays arranged in elongated thin strips so that pixels of the arrays are aligned end to end. Each elongated strip may include from about 25 to about 200 pixels (each being about 65 microns by 55 microns). The detector may be a two-dimensional array of pixels such as with complementary metal-oxide-semiconductor (CMOS) or charge-coupled device (CCD) detector circuitry. Alternatively the photodiode array may consist of several larger individual photodiode elements (about 1 mm×1 mm, or about 3 mm×3 mm) each with one pixel per detection color. The detector may be an array of PIN photodiodes selected to have a fast response time (about 10 ns), large spectral range (covering at least 450 nm to 800 nm), large spectral response (at least 0.1 A/W depending on wavelength), and a small dark current (about 2 nA) to give a rapid and strong optical signal over the visible spectrum with minimal noise. One such PIN detector could be PDB-C134 (Advanced Photonix, Camarillo, Calif.). The array of PIN photodiodes may be arranged in a small grouping (in an area of less than that of about a 15 mm circle) to keep the detection system compact.

Each detector (which may be an array) may monitor one, two, three, or more samples at a time. Each detector may be adapted for moving from sample to sample. The detectors may be arranged to read more than one pixel at a time (from more than one sample). The time between the readings may affect sensitivity due to the entry of light. It may thus be desirable to complete readings as quickly as possible (e.g., less than about 0.5 milliseconds average per pixel per reading) to maximize sensitivity. It may be desirable to complete readings for each pixel in less than 0.1 second, or even less than 0.01 second. It may be desirable to have a final read over all pixels or photodiodes to complete in less than 1 second, less than 0.5 second, or even less than 0.25 second, to be able to precisely match detection with sample temperature and to match detection speed with the speed of the PCR amplification progress.

Alternatively, the detector may include a spectrometer which may also require the use of a prism device or optical diffraction grating to separate light according to different wavelengths. The detector may also include a charge-coupled device or other capacitor containing device or photomultiplier tube.

The ability to excite one or more probes contained within a sample for testing may be enhanced by employing one or more features for controlling the light that is directed to the sample holder from one or more light sources. For example, without limitation, as to light from one or more light source, one or more features may be employed to attenuate, intensify, modulate, collimate, refract, reflect, diffract, or filter such light or any combination of the foregoing.

Consistent with the foregoing, the ability to detect light from one or more excited probes contained within a sample may be enhanced by employing one or more features for controlling the light that is emitted from the sample (or at least one probe therein). For example, without limitation, as to light from a sample, one or more features may be employed to attenuate, intensify, modulate, collimate, refract, reflect, diffract, or filter such light or any combination of the foregoing.

An approach that may be employed for enhancing transmission of light for excitation of one or more probe, for detecting fluorescence emitted by one or more probe or both may involve the selection of a suitable filter arrangement. One or a combination of two or more filters may be employed for this purpose. Selection of a filter for this purpose may be based upon one or more desired attribute of the filter.

The filter arrangement may include a filter wheel including at least one filter pair such that one filter in each pair is an emission filter and one filter in each pair is a detection filter. The instrument may be free of any filter that is both an emission filter and a detection filter. Each filter may allow two or more bands of light wavelengths to pass. The instrument may be free of any filters that allow only a single band of light wavelength to pass. One of each fitter pair may include one filter that is exclusively an emission filter and one filter that is exclusively a detection filter. The instrument may be free of any filters that are not exclusively emission filters or detection filters. The number of filters may match exactly the number of fluorophore classes detected by the instrument. The instrument may be free of any filters that must align with both an emission light path and a detection light path. One or more filters may not align with both an emission light path and a detection light path. All filters may not align with both an emission light path and a detection light path.

In the context of detecting light, it may be expected in some instances that a filter is selected by which a significant amount of light of one or more predetermined wavelengths is allowed transmission through the filter for affording a larger amount of detectable light for a detector. For example, it may be possible that one or more absorptive filter is employed, such as a filter with an optical density (OD) value of about 4, 3, 2, 1 or lower. Successful results may be achieved by the use of one or more filters having an OD value of greater than 4 (e.g., a value of OD 5, OD 6, or OD 7). The cumulative OD value of such filters may be greater than 4 (e.g., a value of OD 5, OD 6, or OD7). The OD values are based upon transmission values measured at a wavelength from about 400 nm to about 800 nm in accordance with a spectrometer according to standard optical metrology transmission measurement techniques (often a custom modified spectrometer is used to measure large optical densities, over about OD 4, and to measure filters with sharp transitions in optical density as a function of wavelength).

The filters may be neutral density filters. They may be uncoated. They may be metallic coated. They may be made of optical quality glass, UV-grade quartz or some other suitable material.

One or more interference filters may be employed for selectively allowing transmission of light within one or more predetermined range of wavelengths, while reflecting light of other wavelengths. For example, one or more dichroic filters may be employed. Examples of suitable dichroic filters may exhibit one or more performance characteristics including transmitting light from the LEDs at the excitation wavelength range(s), and reflecting light at the fluorophore emission wavelength range(s) (or the reverse of reflecting the excitation light and transmitting the emitted light). An example of a suitable dichroic filter employed herein is commercially available from Edmund Optics, Barrington, N.J. under the designation #67-055.

One of more filters may be employed at one or more locations within a system. One or more filters may be employed between a source of light and a waveguide (e.g., a fiber optic structure) through which the light is transmitted. One or more filters may be employed between a light emitting portion of the waveguide (e.g., fiber optic structure) and the sample (and/or holder within which the sample is contained). One or more filters may be employed between the sample (and/or holder within which the sample is contained) and any detector.

One or more components of the system may have a filter assembled to it. One approach may be to select materials for the sample holders of the system herein by which the material intrinsically filters one or more predetermined wavelength or range of wavelengths.

One example of a filter that may be employed herein is a linear variable filter. For example, such a filter may be employed in advance of a detector of the system. Another option that may be employed alone or in combination with a linear variable filter may be to employ one or more bandpass filters or other filter. Examples of suitable bandpass filters may exhibit one or more performance characteristics including a hard coating, at least 90% transmission in the bandpass wavelength range, an optical density of at least OD5 in the blocking wavelength ranges, a transmission band of approximately 10 nm to 150 nm (generally 19 nm to 46 nm), and a sharp transition (less than about 5 nm) between the transmitting wavelengths and the blocked wavelengths. Example dualband bandpass filters may include emission filters with transmission regions of (A) approximately 400 nm to 494 nm and approximately 569 nm to 596 nm; (B) approximately 511 nm to 536 nm and approximately 613 nm to 644 nm; and (C) approximately 540 nm to 559 nm and approximately 660 nm to 680 nm. Each of these dualband filters have wavelengths that correspond generally to the peak wavelengths of the high-powered LEDs. Example dualband bandpass filters may include detection filters with transmission regions of (A) approximately 505 nm to 538 nm and approximately 608 nm to 645 nm; (B) approximately 549 nm to 568 nm and approximately 659 nm to 679 nm; and (C) approximately 572 nm to 598 nm and approximately 695 nm to 730 nm.

Any linear variable filter may be utilized for filtering light such that only light having certain wavelengths can pass through the filter at different filter locations. As a result, only light of a known wavelength may pass through the filter and to the detector (e.g., specific pixels of an array) so that the light that is passing through is a predetermined known wavelength for which only intensity needs to be measured for each pixel in the detector. Examples of suitable linear variable filters may exhibit one or more performance characteristics including a hard-coating, separation of light into a spectral range from about 450 nm to about 800 nm, average transmission of over 40%, and an optical density of at least OD3.

As an alternative to the linear variable filter, a series of discrete bandpass filters may be employed. The bandpass filters may be lined in parallel so that the assembly aligns optically with the detector pixels. In this respect, this embodiment can be simply viewed as a linear variable filter with discrete step-wise portions rather than continuously variable.

As mentioned herein, the detector may be adapted to receive light from a plurality of sources. For example, the detector may receive (e.g., detect) light from a fluorescing sample and light reflected from the light source. Multiple fluorescing agents with different emission wavelengths may be present in the sample. As such, it may be necessary for the detector to be capable of differentiating different colors (e.g., light emanating from different sources and fluorescing agents) so that the software can differentiate data obtained from the fluorescing sample. As a result, it may be beneficial to include one of the filters identified herein. Alternatively, a prism device or optical diffusion grating may be utilized for prismatic separation of the light (which may require detectors that will detect the difference between the light from one or more fluorescing agents and the light from the light source so that data from each can be separated).

As mentioned above, one possible approach is to employ a plural band bandpass filter. The band amount can be selected to correspond generally with the number of light sources of different wavelengths used for excitation of a sample. For example, the employment of a quad-band bandpass filter (if a four light source is employed) may be advantageous. Such a filter may be sized to be within a predetermined size (e.g., covering an area that is only a portion of the total area of the array that defines the detector). For example, a detector may include an array of a predetermined number of pixels adapted for detection. However, the filter may be sized for allowing transmission of light to only a fraction of the pixels (e.g., less than about 75%, less than about 50%, less than about 25%, less than about 10% or even less than about 5% of the pixels) available for detection.

Among the various filter types that may be employed herein are those such as hot mirrors, heat absorbing glass, shortpass filters, longpass filters, infrared cutoff filters, and wide bandwidth bandpass filters.

Filters herein may have a first face, a generally opposing (e.g., generally parallel) second face, and a periphery that typically spans between the first and second face. It is possible that one or more of any of the filters herein may be at least partially encapsulated (e.g., about at least a portion of its periphery) by a material that differs from the filter. One or more of any of the filters may include a suitable filter alignment holder. Such holder may be adapted to attach to one or more of the other components of the system. For instance, the holder may be sized and configured to receive one or more filters, and may also include an attachment portion (e.g., as part of and/or adjoining a peripheral portion of the holder) that includes suitable structure for attaching the holder within the system. For example, the holder may be such that it can be positioned between a light source and a sample holder, between a sample holder and a detector, or both.

The waveguide may be arranged so that a terminal end interfaces with the detector and will be shaped to coincide with the structure of the photodiode array as discussed above. The instrument may include a manifold assembly that connects with the printed circuit board that carries the light source (e.g., the LEDs), and includes passages. These passages may allow for isolation of the individual light source assemblies and may be adapted to receive the waveguide (e.g., fiber bundles).

The instrument may include a housing for receiving the waveguide. The housing may include an upper portion that is adapted to fit in between the heat exchangers and to be aligned with (and located below) a sample holder. The housing may include one or more projections for aiding in aligning the housing within the instrument. The housing may also include one or more mounting flanges to provide a surface for attaching to a cavity within the instrument. The housing may further include a base portion having a cavity defined therein through which one or both fork portions of the bifurcated waveguide (e.g., fiber optic bundles) are passed, and which can receive a resin for potting the waveguide. A bottom cover portion may be adapted to interface with the detector and may be located above the printed circuit board and detector located thereon. One or more ports may also be formed along a surface of the housing so that the one or more ports align with the light source. The light source may penetrate through the ports or alternatively may remain adjacent to the ports without penetrating the ports. There may be an optical filter (such as a bandpass filter) between the light source and the penetrating ports.

Figure 2:
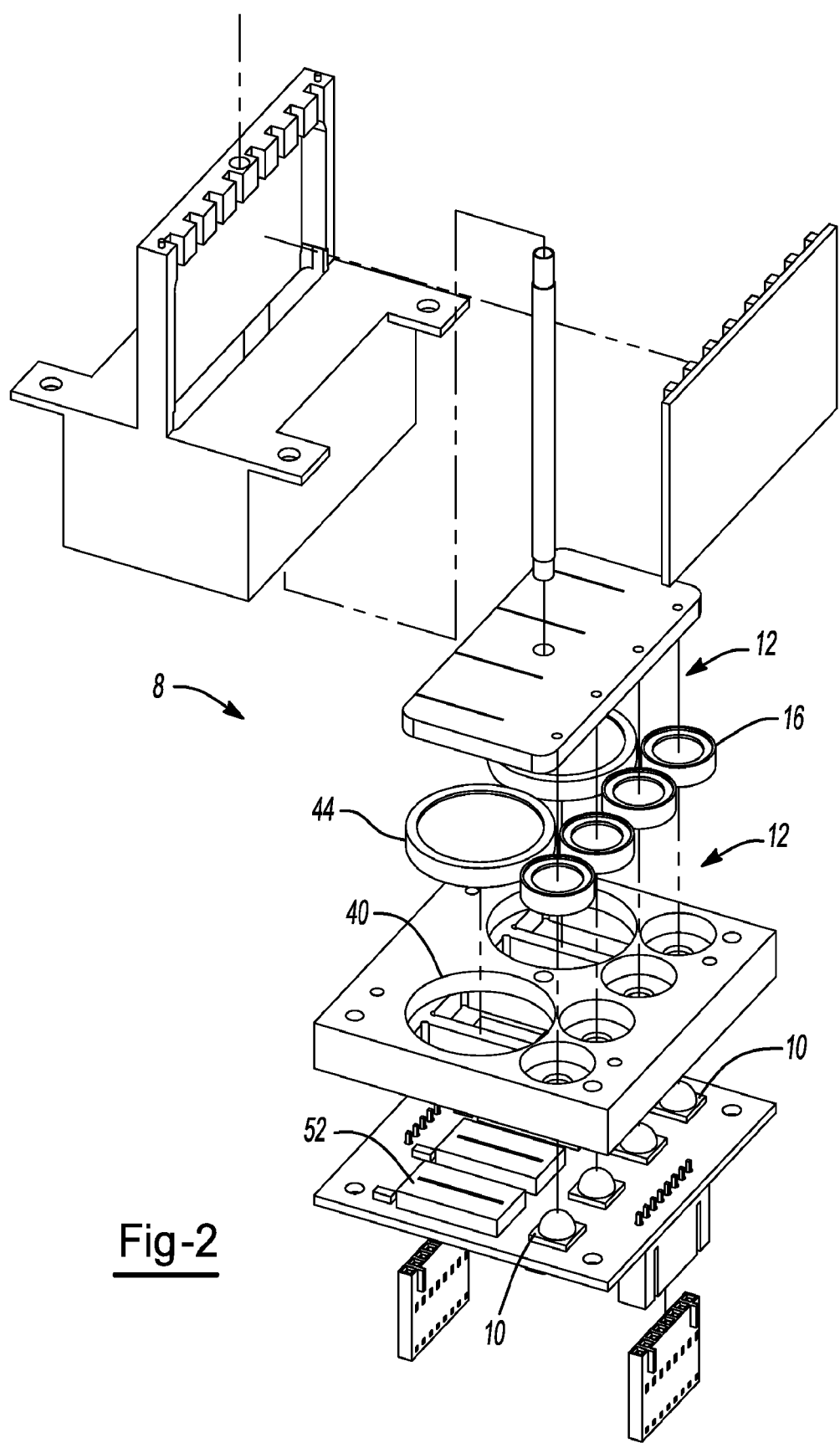
FIG. 2 is an exploded view of an illustrative real-time cycling module in accordance with the present teachings.
Figure 3:
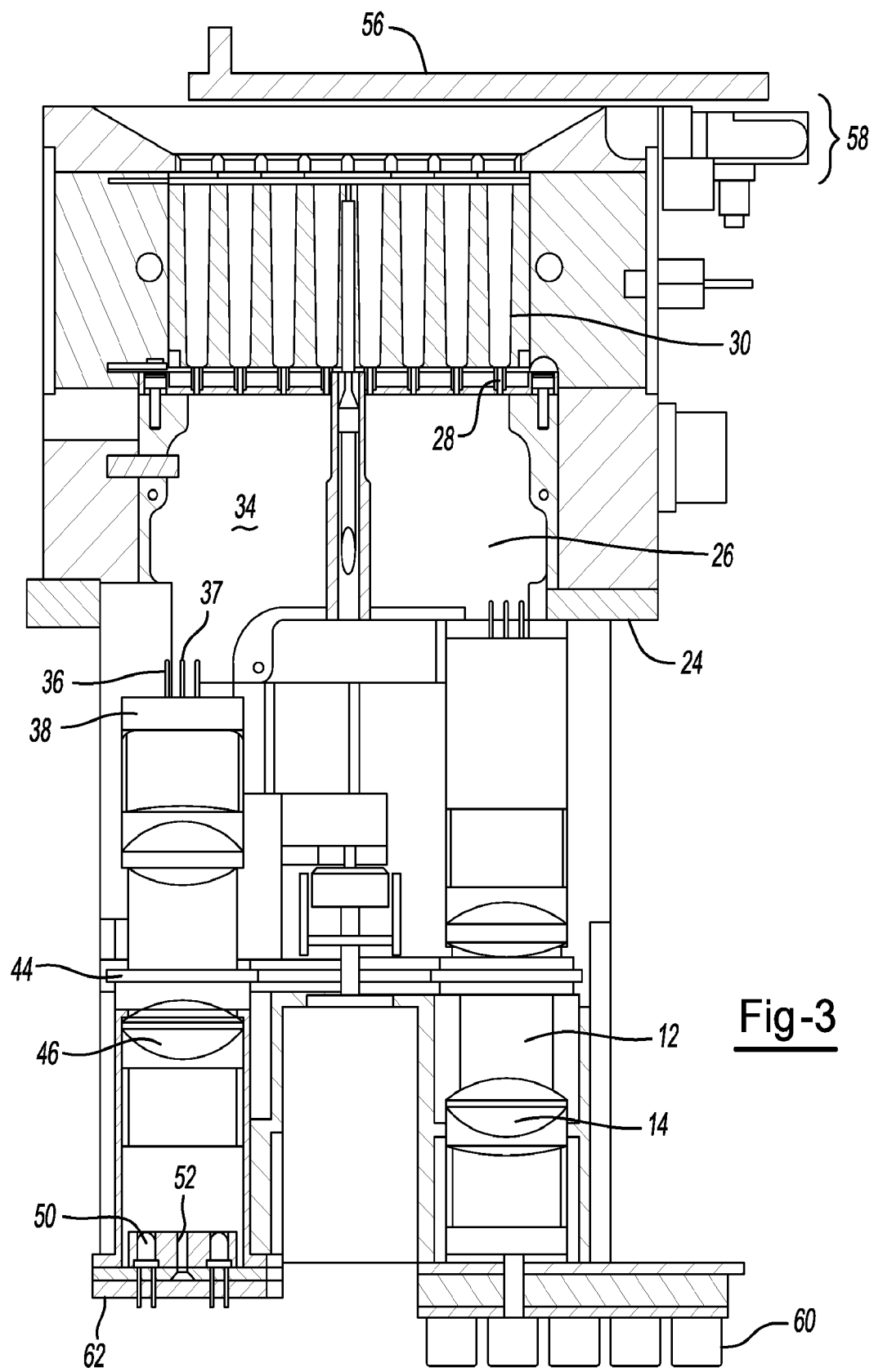
FIG. 3 is an additional side cutaway view of an illustrative real-time cycling module in accordance with the present teachings.
Figure 4:
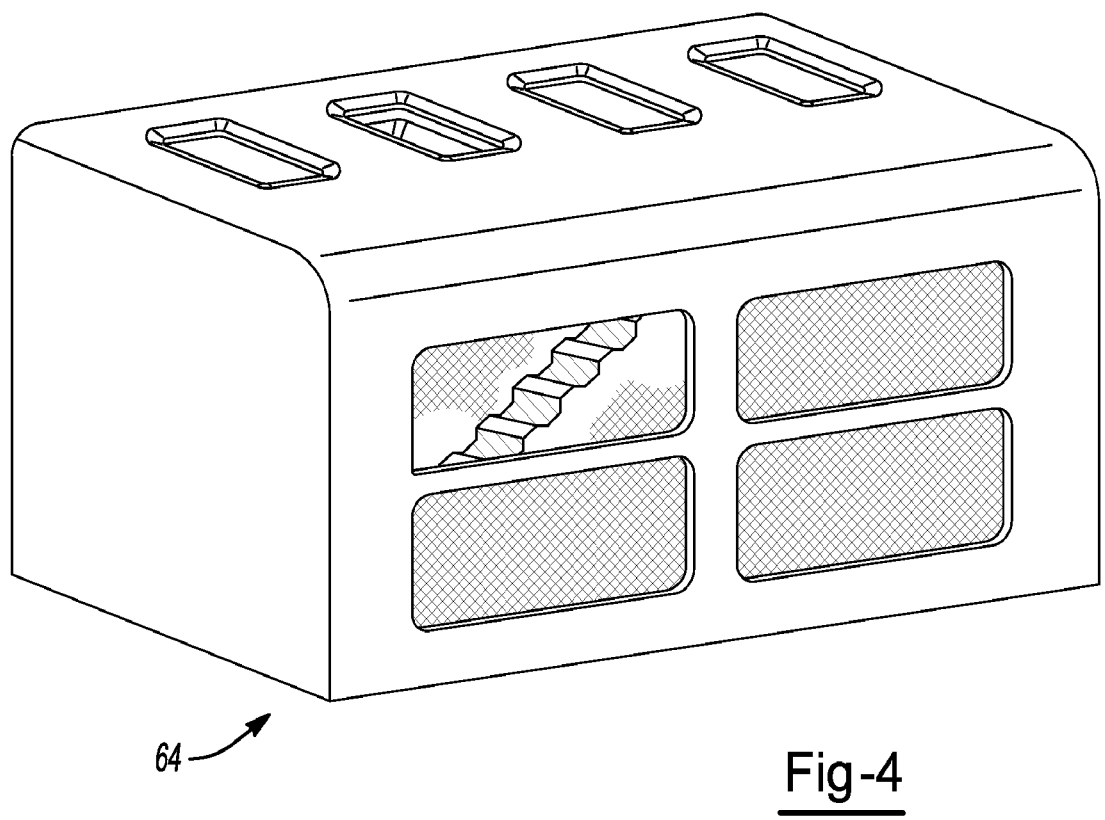
FIG. 4 is a perspective view of an exemplary external housing in accordance with the present teachings.

FIGS. 1-3 show views of exemplary qPCT modules as described herein. FIG. 1 shows a cutaway view of a qPCR module 8. FIG. 2 shows an exploded view of a qPCT module 8. The housing for the qPCR module may include one or more cover portions for enclosing the entirety of the module. Alternatively, one cover portion 64 (see FIG. 4) may house and enclose a plurality of modules. A light blocking lid 56 may be included, in addition to detection switch 58 for notifying a user that the lid is open. An array of one or more light sources 10 emit excitation light that travels along an excitation light path 12. The light source array may consist of two rows of three LEDs (Innovations In Optics and/or Philips Lumileds) in a first excitation light pattern 11. Each LED may emit a different peak light wavelength selected to excite an array of different fluorophores in one or more samples 32. One such grouping may include six Luxeon Z LEDs with wavelength peaks of approximately 477.5 nm, 527.5 nm, 532.5 nm, 588.5 nm, 630.0 nm, and 660.0 nm (all peaks ±10 nm due to normal LED manufacturing variation). A heat sink 60 may be located adjacent the one or more light sources for any heat produced by the light source 10. A friction fit lens holder 13 holds a first excitation doublet lens 14 which creates an excitation light path which is approximately collimated along the axis of the excitation light path 12. One such first excitation doublet lens 14 may be from Edmund Optics #49-956, #49-932, or a similar lens. Collimated light may be necessary to achieve the optimum light filtering by the excitation filter 16 including filtering with optical densities of over OD4 for undesired light wavelengths, optical densities of less than 0.1 for desired light wavelengths, and a sharp transition between the desired and undesired wavelengths. Excitation filter 16 has at least one waveband of light that is allowed to pass through the filter. The start and stop wavelengths of the wavelength bands are designed to work well with the light sources 10 and the desired fluorophores in one or more samples 32. The use of a multiband excitation filter 16 allows for multiple fluorophores to be detected simultaneously. One or more single band or multiband excitation filters 16 are attached to a movable filter wheel 18. The movable filter wheel 18 allows for one or more excitation filter 16 to be used to refine the wavelengths of light that excites the fluorophores in one or more samples 32. The filter wheel is moveable while the one or more samples 32 remain fixed. Example multiband excitation filters may include transmission regions of (A) approximately 400 nm to 494 nm and approximately 569 nm to 596 nm; (B) approximately 511 nm to 536 nm and approximately 613 nm to 644 nm; and (C) approximately 540 nm to 559 nm and approximately 660 nm to 680 nm.

The collimated filtered excitation light continues along the excitation beam path 12 to a second doublet lens 20 which is held in place by another friction fit lens holder 13. The second doublet lens 20 may be the same model as the first excitation doublet lens 14 or may be slightly modified to adjust the focal length such as Edmund Optics #49-350. The second excitation doublet lens 20 refocuses the excitation light onto an excitation plate 22. Due to symmetry and placement of the excitation doublet lenses 14 and 20, multiple individual light spots will shine on the excitation plate 22 in a second emission light pattern 23 which is a roughly mirrored version of the first excitation light pattern 11 of the light sources 10. An array of excitation fiber optic bundles 24 are mounted flush with the excitation plate 22 and are centered on the individual light spots on the excitation plate. The second doublet lens 20 is designed with a specific focal length and is placed at the proper distance from the excitation plate 22 such that the excitation light is at an angle that is at or below the acceptance angle of the fiber optics in the bundles 24. The filtered excitation light travels through fiber optic bundles in the fiber optic manifold 26 to sample alignment ports 28. The sample alignment ports 28 align the fiber optic bundles 24 underneath each and every sample 32 in a way that light exits the fiber optic bundles 24 substantially along the vertical axis of the samples 32. Samples 32 have an optically transparent bottom end 33 which is designed to maximize the amount of light transmitted through the bottom while minimizing the amount of light that is reflected from the sample bottom. Each sample 32 has at least one fiber optic cable from each light spot on the excitation plate 22. Thus each sample 32 can be excited by each light source in the light source array 10.

Each light in the light source array 10 can be individually controlled (to be set full off, full on, or on at multiple power levels) to provide multiple different light colors. Each excitation filter 16 in the movable filter holder 18 can pass at least one color waveband. By selectively operating one or more of the light sources 10, and by selectively moving the excitation light filters 16 into the excitation light path 12, multiple fluorophores can be optimally excited in samples 32.

The fluorophores in the sample 32 have a Stokes shift in which the fluorophores emit light at a wavelength that is shifted in wavelength from the light that excited the fluorophore. The quantity of emitted light depends on the properties of the chemicals in the sample 32. For example, the quantity of emitted light may be proportional to the amount of PCR-amplified DNA in the sample 32. As the sample holder 30 undergoes temperature cycling, PCR may amplify the quantity of initial DNA in sample 32. Thus the progress of a process, such as PCR amplification, can be monitored if the magnitude of the various emitted wavelengths can be detected. The magnitude of that emitted light and the correlation of that light magnitude to the PCR cycle number can be used to measure the initial amount of DNA, if any, in the sample.

Some of the light emitted from at least one fluorophore in the sample 32 will pass through the optically transparent sample bottom end 33 and to the sample alignment ports 28 at the bottom of the sample holder. A set of emission fiber optic bundles 36 carries the emitted light from each sample through the fiber optic manifold 26 along the detection side 34. Each of the emission fiber optic bundles 36 may be a set of many small diameter optic fibers, or may comprise of a single large diameter optic fiber of approximately 1 mm diameter. The emission fiber optic bundles 36 are mounted to an emission plate 38 which has holes in a first emission light pattern 39 to accept the emission fiber optic bundles. The emitted light shines out of the emission fiber optic bundles through emission light path 40. A doublet emission lens 42, held in place by lens holder 13, forms the emission light into approximately collimated light along the axis of the emission light path 40. At least one emission filter 44 is mounted to movable filter holder 18. Each emission filter 44 may allow one or more light wavebands to pass with high optical density outside of the wavebands and low optical density within the wavebands. The starting and stopping wavelengths are designed to filter out stray excitation light from light sources 10 which may reflect back from the samples 32, or any other stray light such as infrared light generated by the thermally controlled samples or other components of the qPCR module 8, while allowing for maximum transmission of the expected emitted light from the fluorophores in the samples. Emission filters 44 are aligned with excitation filters 16 on the movable filter holder 18 in order to pair the appropriate emission filter 44 with the appropriate excitation filter 16 for each fluorophore. The light color(s) from the light source array 10, waveband(s) of excitation filter 16, fluorophore(s) in sample 32, and waveband(s) of emission filter 44 comprise at least one set which have been designed to work together to optimize the signal to noise ratio of the detected light emitted from the fluorophore, maximize the signal strength of the desired fluorophore, and minimize the unwanted signals from other fluorophores in the sample 32. Example multiband emission filters may include transmission regions of (A) approximately 505 nm to 538 nm and approximately 608 nm to 645 nm; (B) approximately 549 nm to 568 nm and approximately 659 nm to 679 nm; and (C) approximately 572 nm to 598 nm and approximately 695 nm to 730 nm.

The filtered collimated light is refocused by emission doublet lens 46 onto photodiode array holder 48 with the resulting second emission light pattern 54 that approximately mirrors the a first emission light pattern 39 of emission fiber optic bundles 36 in emission plate 38. The photodiode array holder 48 is configured to hold at least one photodiode detector in a photodiode detector array 50 such that each photodiode detector receives light which is almost exclusively from a different sample 32. If eight samples 32 are used as shown in FIG. 1, then at least eight photodiode detectors 50 may be used to detect light from each sample simultaneously.

An additional photodiode detector 52 may be placed into the instrument near the photodiode detector array 50 for purposes of providing a check on the output of the light source 10. This additional photodiode detector 52 aligns with an additional light check opening on the emission plate 38. A light check fiber optic bundle 37 is placed in the emission plate 38 and then the light check fiber optic bundle passes through the fiber optic manifold 26. Alternatively, an additional photodiode detector 52 may be placed near the fiber optic manifold 26, bypassing the emission light path 40 and associated doublet emission lenses 42 and 46, in order to minimize the light that might cross contaminate the desired second emission light pattern 54. A light blocker 62 may be included to prevent any light from outside the device from being detected inadvertently. The light check fiber optic bundle 37 splits into at least one branch at the light check fiber branch region 34. This branched light check fiber optic bundle 37 goes to each individual light spot on the excitation plate 22. Thus the light output of each light source 10 can be detected individually by the additional photodiode detector 52. The quantity of electric current that is used to operate the light sources 10 can be adjusted to maintain a constant light signal on the photodiode detector 52. Alternatively, the additional photodiode detector 52 signal can be used to adjust the optical read time for the photodiode detector array 50 in order to maintain detection signal strength. This adjustment can be done on an as-needed basis to adjust for differences in light output and to adjust for detection strength which may both vary with age, use, and temperature.

As to all of the foregoing general teachings, as used herein, unless otherwise stated, the teachings envision that any member of a genus (list) may be excluded from the genus; and/or any member of a Markush grouping may be excluded from the grouping.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Invention of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. Concentrations of ingredients identified in Tables herein may vary ±10%, or even 20% or more and remain within the teachings.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. An instrument for performing polymerase chain reaction with real-time detection comprising:
   a. a sample holder configured to receive one or more samples that each have at least one portion that is generally optically transparent, and that receives a biological sample comprising a nucleic acid to be amplified and at least one fluorescing agent that interacts with the nucleic acid during amplification and that emits light upon excitation by light of a known wavelength;
   b. at least one light emitting diode device that is carried on at least one support substrate and is in electrical communication with a power source, and is adapted to emit light at a plurality of different wavelengths along an excitation path and arranged to emit light in a light pattern;
   c. at least one photodiode array detector adapted to issue signals based upon intensity of light it receives; and
   d. a filter wheel including at least one filter pair such that one filter in each pair is an emission filter and one filter in each pair is an excitation filter, the filter wheel being configured to be rotated relative to the at least one light emitting diode device to selectively align the excitation filter to be within the excitation path of the at least one light emitting diode device;
   e. an array of fiber optic bundles, each of the fiber optic bundles having a first end aligned with a light spot of the light pattern of the at least one light emitting diode device and a second end aligned with one of the samples.

2. The instrument of claim 1, wherein the photodiode array detector reads fluorescence emitted by the fluorescing agent in less than 0.1 second.

3. The instrument of claim 1, wherein the photodiode array detector reads fluorescence emitted by the fluorescing agent in the range of less than 0.01 second.

4. The instrument of claim 1, wherein the sample holder is sandwiched between opposing thermoelectric devices.

5. The instrument of claim 1, wherein each filter allows two or more bands of light wavelengths to pass.

6. The instrument of claim 1, wherein the instrument simultaneously detects light at multiple wavelengths.

7. The instrument of claim 1, wherein the filter wheel is configured such that alignment of the excitation filter in the excitation path further aligns the emission filter to be within an emission path of light emitted from the at least one fluorescing agent.

8. The instrument of claim 1, wherein the at least one light emitting diode device comprises a plurality of light emitting diode devices, wherein the filter wheel is configured to be rotated relative to the plurality of light emitting diode devices.

9. The instrument of claim 8, further comprising a first excitation lens disposed within the excitation path, wherein the filter wheel is configured to be rotated relative to the first excitation lens.

10. The instrument of claim 9, further comprising a second excitation lens disposed within the excitation path, the second excitation lens disposed on an opposite side of the filter wheel as the first excitation lens.

11. The instrument of claim 10, wherein the plurality of light emitting diode devices are arranged to emit light in a first excitation light pattern, wherein the first excitation lens, the excitation filter, and the second excitation lens are configured to effect the light emitted by the plurality of light emitting diode devices to produce a second excitation light pattern when the light passes therethough, the second excitation light pattern being mirrored to the first excitation light pattern.

12. The instrument of claim 11, wherein each of the fiber optic bundles has a first end aligned with a light spot of the second emission light pattern and a second end aligned with one of the samples.

13. The instrument of claim 12, wherein each fiber optic bundle of the array of fiber optic bundles includes at least one fiber optic cable aligned with each of the samples.

14. The instrument of claim 10, further comprising first and second emission lenses disposed within an emission path of light emitted from the at least one fluorescing agent, the first and second emission lenses opposing one another on opposite sides of the filter wheel; and wherein the filter wheel is configured to be rotated relative to the first and second emission lenses.

15. The instrument of claim 1, wherein the photodiode array detector reads fluorescence emitted by the fluorescing agent in less than 0.25 second.

* * * * *